(12) United States Patent
Ferzli et al.

(10) Patent No.: US 8,934,636 B2
(45) Date of Patent: Jan. 13, 2015

(54) STETHOSCOPE, STETHOSCOPE ATTACHMENT AND COLLECTED DATA ANALYSIS METHOD AND SYSTEM

(76) Inventors: George S. Ferzli, Staten Island, NY (US); George Ferzli, Jr., Staten Island, NY (US)

( * ) Notice: Subject to any disclaimer, the term of this patent is extended or adjusted under 35 U.S.C. 154(b) by 514 days.

(21) Appl. No.: 12/924,902

(22) Filed: Oct. 7, 2010

(65) Prior Publication Data

US 2011/0087135 A1 Apr. 14, 2011

Related U.S. Application Data

(60) Provisional application No. 61/278,672, filed on Oct. 9, 2009, provisional application No. 61/296,746, filed on Jan. 20, 2010.

(51) Int. Cl.
*A61B 7/04* (2006.01)
*G06F 19/00* (2011.01)

(52) U.S. Cl.
CPC ............... *A61B 7/04* (2013.01); *G06F 19/345* (2013.01)
USPC ............................. 381/67; 600/528; 600/586

(58) Field of Classification Search
USPC ............................. 381/67; 600/300, 528, 586
See application file for complete search history.

(56) References Cited

U.S. PATENT DOCUMENTS

| 7,133,715 | B1 * | 11/2006 | Smits et al. | 600/544 |
|---|---|---|---|---|
| 7,346,174 | B1 * | 3/2008 | Smith | 381/67 |
| 8,344,233 | B2 * | 1/2013 | Cai et al. | 84/602 |
| 2003/0139671 | A1 * | 7/2003 | Walston et al. | 600/437 |
| 2004/0076303 | A1 * | 4/2004 | Vyshedskly et al. | 381/67 |
| 2006/0098825 | A1 * | 5/2006 | Katz | 381/67 |
| 2008/0075316 | A1 * | 3/2008 | Chan | 381/381 |
| 2008/0298603 | A1 * | 12/2008 | Smith | 381/67 |
| 2009/0257600 | A1 * | 10/2009 | Dorfman et al. | 381/58 |
| 2011/0096936 | A1 * | 4/2011 | Gass | 381/67 |

* cited by examiner

*Primary Examiner* — Disler Paul
(74) *Attorney, Agent, or Firm* — Gottlieb, Rackman & Reisman, P.C.

(57) ABSTRACT

A device for converting acoustic data collected by a stethoscope into digital data for transmission to a processor for storage and/or comparison with data stored in a database, and to optionally provide computer generated suggestions for diagnosis, is provided in the form of an in-line device interposable between a head of the stethoscope and an acoustic transmission portion of the stethoscope, or is integral with the head, and advantageously has the appearance of an icon of pleasing appearance, for example, a butterfly, in which are incorporated the structural requisites of a functioning stethoscope and/or capabilities for receiving and transmitting to a diagnostician, audio signals gathered from patient examination, and optionally also other data collected at examination and/or following the examination. The butterfly-shaped device, includes a central body advantageously serving as a conduit for transmitting sound received from the patient to the physician or a remote system for analysis and diagnosis.

13 Claims, 14 Drawing Sheets

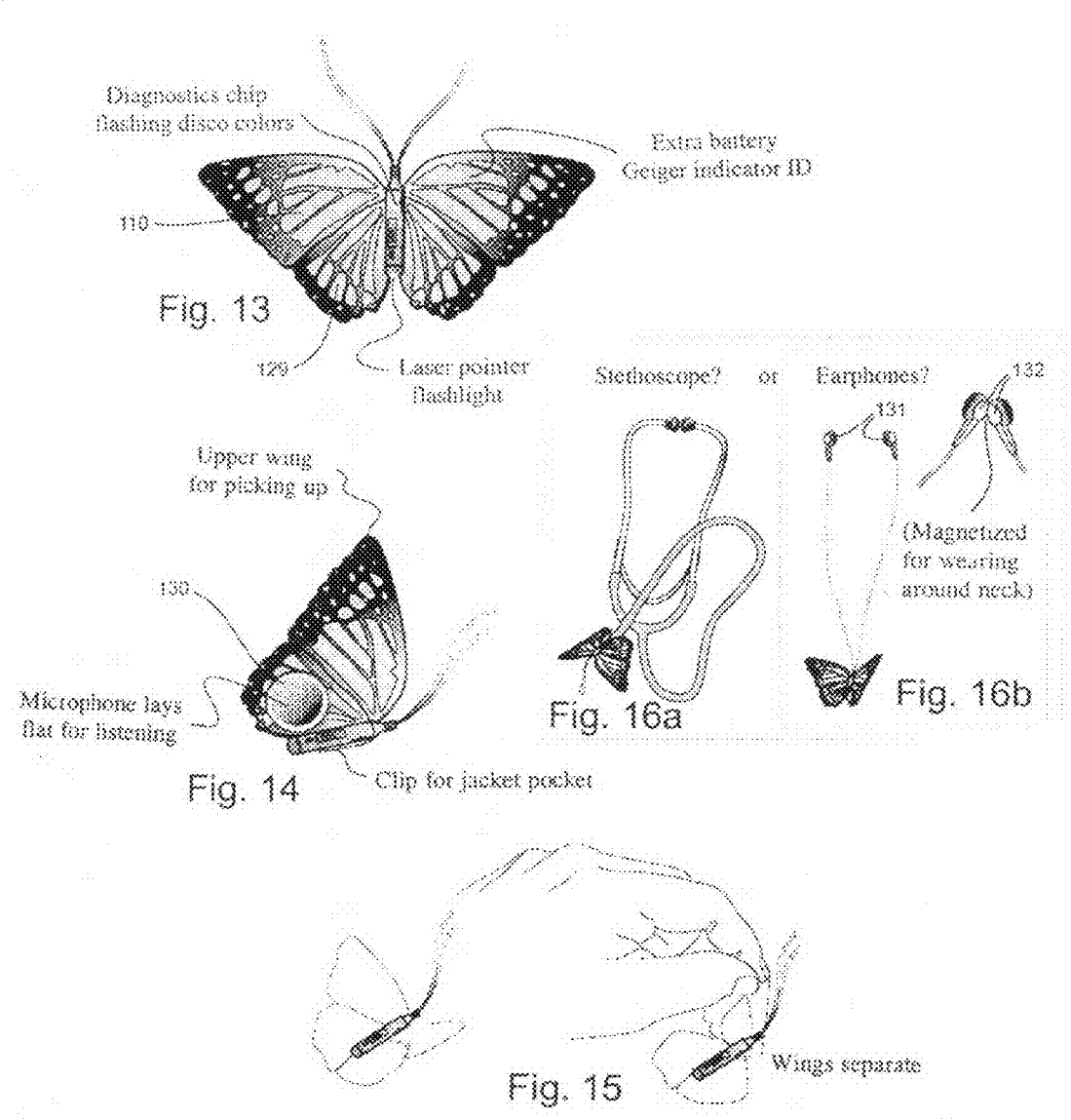

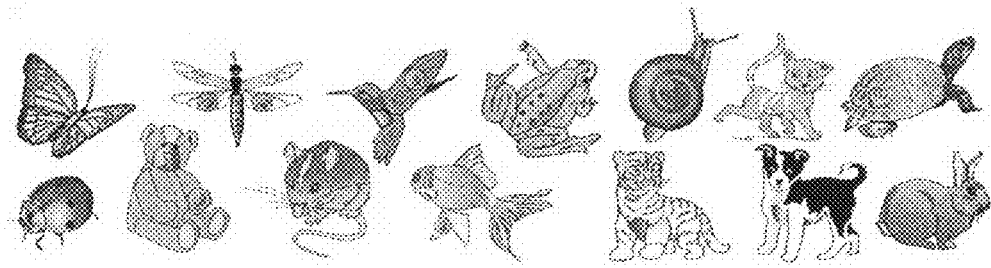
Fig. 17
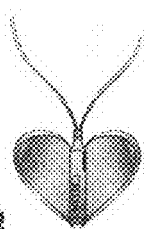
Fig. 18
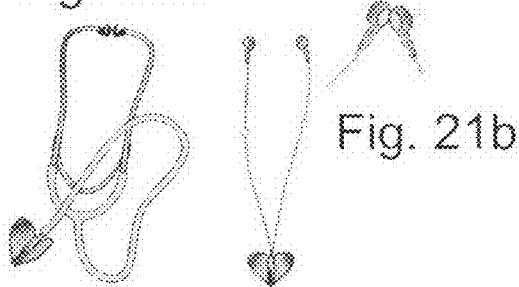
Fig. 21a
Fig. 21b
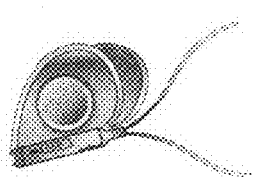
Fig. 19
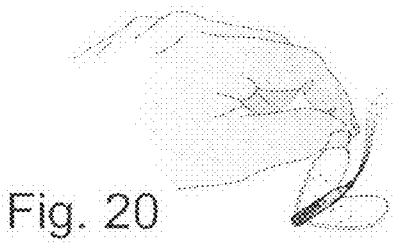
Fig. 20

STETHOSCOPE, STETHOSCOPE ATTACHMENT AND COLLECTED DATA ANALYSIS METHOD AND SYSTEM

BACKGROUND OF THE INVENTION

The present invention relates to a stethoscope. More particularly, the invention relates to a stethoscope and an attachment portion for a stethoscope providing improved analysis capabilities, and advantageously being embodied in a structure presenting enhanced appearance and function, in a form particularly well suited for use in pediatric medicine.

The acoustic stethoscope remains the most widely used auscultation device in both developed and developing medical economies. The basic design references the 1978 Patent held by 3M for production of the Littmann Stethoscope.

Developments over the well accepted acoustic stethoscope design have been suggested, including electronic stethoscope designs. However, the international adoption of heretofore-suggested electronic stethoscopes has been slow and cumbersome, their general failure points being cost, required change of habit and potential distortion of the acoustic auscultation process.

While effective as a monitoring and diagnostic tool, the stethoscope relies upon the analysis of the diagnostician listening to the sound collected by the stethoscope, i.e., the subjective judgement of the physician, himself or herself. Attendant with this drawback is the possibility that the physician listening to the sounds detected by the stethoscope may mis-diagnose, or miss entirely, an ailment from which the patient is suffering.

Additionally, while quite effective as a monitoring and diagnostic tool, the well known stethoscope of conventional design projects a somewhat cold and clinical appearance that may trigger anxiety in a patient, especially in a young patient undergoing medical care and/or observation.

An object of the invention is to provide a low cost alternative to an electronic stethoscope, by applying a synergistic utilization of current technologies, to develop a novel audio capturing device, advantageously interfacing through a device agnostic communication protocol, that can be easily integrated with available mobile and stationary diagnostic equipment.

It is a further object of the invention to provide the above features in a manner which is supported by proprietary mobile and desktop dashboard applications used for the interpretation of diagnostic queries and the consumption of Rich Diagnostic Content (RDC)

A still further object of the invention is to provide a stethoscope, at least a portion of which having an appearance which is reassuring to the patient, particularly a pediatric patient, such that a calming effect is achieved during patient examination, and which optionally concomitantly provides multiple functions with coordinated synergistic benefits and effects, to aid in diagnostic evaluation.

SUMMARY OF THE INVENTION

These and other objects of the invention are achieved by utilizing a system operable to augment, inform and optionally automate diagnostic processes performed with any stethoscope, an optionally usable in combination with a basic stethoscope of conventional design.

The objects are further implemented in a stethoscope design embodied broadly in a device having a stethoscope head or in-line audio capture and analog/digital conversion device presenting a general appearance, at least suggestive of, an animal, character or icon of pleasing appearance and impression, advantageously one with wing-like structure, for example, a butterfly, in which are incorporated the structural requisites of a functioning stethoscope and optionally, auxiliary capabilities for receiving and transmitting to a diagnostician, audio signals gathered from patient examination, and/or other data collected at examination and/or following the examination.

According to a feature of the invention, an acoustic fingerprint or signature of the sound sensed by a stethoscope probe is matched against an existing database of stored acoustic fingerprints associated with known conditions. The communication between the source and the database is optionally platform agnostic, or could be tied to proprietary transmission technology. The system disclosed herein would advantageously use, for example, a three step process to record, query, then report or "tag" any given acoustic passage.

A multi-party system comprising hardware, proprietary software applications, and a proprietary database server application is advantageously utilized. In a particularly advantageous embodiment, an in-line electronic recording device is presented, which captures sound from along a conventional stethoscope tube during diagnostic procedures. The recording device would further optionally allow for the recording of examiner audio notes and the capturing of patient subject photos or videos for identity verification and further diagnostic studies as part of an integrated patient record. The construction of the in-line device according to an embodiment of the invention advantageously allows for a customizable fit, making it suitable as a simple enhancement for the majority of conventional acoustic stethoscopes. The in-line device is also optionally equipped with a low-power wireless transceiver, which allows it to offload its data to a device upstream.

The aforementioned upstream device can be any mobile or stationary computing node capable of connecting to a database server application, for example, over TCP/IP network. The device is also advantageously configured to be capable of presenting rich digital media and displaying interactive analytical reports.

In accordance with an embodiment of the invention, recorded audio data from the stethoscope is processed by proprietary software running on both the local computing node and at the server level, in order to determine information relevant to diagnosis. A response is then returned from the server to the local computing node, where the basic diagnostic result can be augmented by the presentation of Rich Diagnostic Content, also pulled from the networked database. Rich Diagnostic Content may, for example, include video, audio, images, documents, hyperlinks, or other digital media of relevance to a medical diagnosis made with the enhanced stethoscope system. Captured, classified and diagnostic content is presented in a unique digital patient record for use in multi-format viewing.

A verified database is provided as part of the system, and differs, for example, from a known music database, in that a music track's audio fingerprint is implicit, and is only affected by ambient noise during the recording phase. In the case of this invention, a large sampling of patient auscultation sounds, normal and abnormal, advantageously needs to be aggregated, classified and enhanced through ongoing learning. The invention includes, but is not exclusive to, the design of a learning algorithm for the diagnostic classifier, utilizing machine learning code to interpret and expand the database functionality using successfully logged audio "fingerprints."

In accordance with a particularly advantageous embodiment of the invention, the head of the stethoscope (chest-piece) will assume the general shape or suggested appearance of an appealing animal or character, for example, a butterfly, with the "central body" of the animal representation advantageously serving, inter alia, as a conduit for transmitting sound received from the patient to the physician for analysis and diagnosis, as described above herein.

In accordance with this embodiment, one end of the central body can be optionally connected to electronic ear phones (buds) or to an input of another device (digital analysis version) or to the ear piece of a regular stethoscope (analog version).

In an embodiment in which the animal depiction for the stethoscope head has wings, the wings would serve advantageously to house structural components in a convenient manner. The wings could be structurally configured to further facilitate handleablility by the user. For example, in the example of a butterfly, upper ones of the wings (larger ones closer to the head) could be configured to advantageously flip upward to facilitate grasping of the device. The wings could optionally have a built-in space within them for receiving other components. For example, they may be used as a small storage space for batteries, to accommodate a small radiation (Geiger-like) detector, and/or to display a logo, a name, an ID, an animated light, etc., via an appropriate visual output device, such as an LCD display.

The rear ones of the wings (smaller ones closer to a rear of the central body) are advantageously configured to accommodate one or more sound detectors. These wings advantageously remain flat, so as to rest against the body part being monitored (chest, heart area, abdomen, etc.).

In an analog version of the stethoscope according to an embodiment of the invention, the underside of these rear and upper wings advantageously carry, or include, a high frequency membrane and a low frequency membrane, respectively (alternatively, the rear wings can carry the low frequency membrane and the upper wings can carry the high frequency membrane. In that case, the upper wings will also remain flat, and the device can be held with a ring device or other suitable structural adaptation carried or attached to, for example, an anterior part of the central body). The sound would then, for example, be transmitted directly from the rear wings to the body from the lateral sides of the body.

Alternatively, in accordance with a digital embodiment, the listening device would comprise one or more microphones having suitable sensitivity and frequency ranges, which capture the patient sounds as electronic audio signals.

It is contemplated that the stethoscope according to an embodiment of the invention can be suitably configured as an in-line device for use with an acoustic earpiece of a standard (conventional) acoustic stethoscope, in which case, if the sounds are captured by electronic means, such as with a microphone, the in-line device will additionally include a speaker or other digital-to-audio convertor, for reproducing the electronic data into audio so that the physician can hear the sounds, while advantageously simultaneously recording and/or sending the electronic data for analysis and/or storage for future use.

Alternatively, a specially configured butterfly (or any generic animal/character-shaped) audio sensor assembly can send electronic information to ear buds which convert the data to audible sound.

An embodiment of the invention will be exemplified with reference to a butterfly shaped stethoscope with novel and advantageous symmetric chamber design, as described below. This will act as a passthrough sound device preserving an original acoustic signal. The signal is advantageously recorded with a stereo MicroElectrical-Mechanical System (MEMS) microphone unit on either side of the sound path.

The components advantageously comprise the following, alternatively or in selective combination (described relative to the butterfly example):

Sound Chambers

High Frequency (Traditionally Cold Ring and Membrane)

The rear "wing" structures (smaller wings of the butterfly form) advantageously form a continuous cold ring and membrane structure that has a concave surface facing towards the patient contact area. The membranes are vibrated in stereo as sound is pushed to the sound path past the MicroElectrical-Mechanical System (MEMS) microphones and into the plastic tubing leading to the physician's or diagnostician's ears.

The MEMS microphone, which is advantageously employed in the preferred practice of the invention at the present state of the art, is also called a microphone chip or silicon microphone. The pressure-sensitive diaphragm is etched directly into a silicon chip, and can advantageously be accompanied with an integrated pre-amplifier. An advantage of MEMS microphone technology is that built in analog-to-digital converter (ADC) circuits can be incorporated on a common CMOS chip, providing the function of a digital microphone, thereby permitting facilitated integration with other digital circuitry.

Low Frequency (Traditionally Hollow Metal Cup, Skin Forms Membrane)

The rear of the rear and/or upper wing structures will advantageously contain geometry to allow for low frequency auscultation. The low frequency sound path merges with the main sound path from where the signal is recorded, and the sound wave transmitted to the consultants ears.

Sound Path

The sound path is shaped and/or adapted to connect to either a stethoscope tube (analog type) or, conveniently to, for example, a 3.5 mm headphone jack (digital type). This requires a pass through chamber around the headphone jack to alleviate air pressure and allow for versatility of sound review. The headphone jack is optionally connected to an on-chip amplifier and built-in recorded storage, allowing for instant replay and wireless transmission. The sound path can exit on the rear end, or the front of the butterfly structure, as shown in the alternative diagrams.

Battery

Dual batteries are advantageously housed within the larger front wings. These can be, for example, standard lithium ion batteries or rechargeable lithium polymer batteries. Charging pins are provided in the case of rechargeable batteries in a suitable position, for example, located on the underside of the body. These will allow for convenient recharging of the device, for example, on a desktop stand or by connection with a portable adapter.

Camera

Optionally, a small digital camera is provided on the underside of the butterfly "belly" that allows for documentation and storage of time stamped patient photographs for verification and Electronic Medical Record (EMR) tie-in purposes.

It is believed that the camera represents a major advance, and it is contemplated that it may one day become mandated as a basis for any documentation in any EMR. For this reason, this advance is considered to be a particularly advantageous option of the invention.

BRIEF DESCRIPTION OF THE DRAWINGS

FIGS. 11a and 11b are perspective views of another embodiment directed to a clip-on camera for attachment to a conventional stethoscope;

FIG. 13 is a plan view of another embodiment of the device according to the invention having a butterfly form;

FIG. 14 is a side elevational view of the embodiment of FIG. 13;

FIG. 15 is an explanatory view of the embodiment of FIGS. 13 and 14;

FIGS. 16a and 16b are respective depictions exemplifying alternative forms of a stethoscope incorporating the embodiment of FIGS. 13 and 14;

FIG. 17 illustrates examples of a few possible representations that can be adopted in configuring a stethoscope head or in-line device in accordance with an embodiment of the invention;

FIG. 18 is a plan view of a another embodiment of the device according to the invention directed to a heart-shaped icon form;

FIG. 19 is a side perspective view of the embodiment of FIG. 18;

FIG. 20 is an explanatory view of the embodiment of FIGS. 18 and 19;

FIGS. 21a and 21b are respective depictions exemplifying alternative forms of a stethoscope incorporating the embodiment of FIGS. 18 and 19.

DETAILED DESCRIPTION OF THE INVENTION

An advantageous feature of the invention is to capture acoustic data during the auscultation process by transforming data collected by a standard acoustic stethoscope, advantageously without altering the enclosed sound pipe and resulting wave-based transmission from the membrane to the examiner's or diagnostician's ears.

A second advantageous feature provides the ability to capture patient identification and examiner's audio notes during consultation through optionally externally facing sensors on the unit housing.

Figure 1:
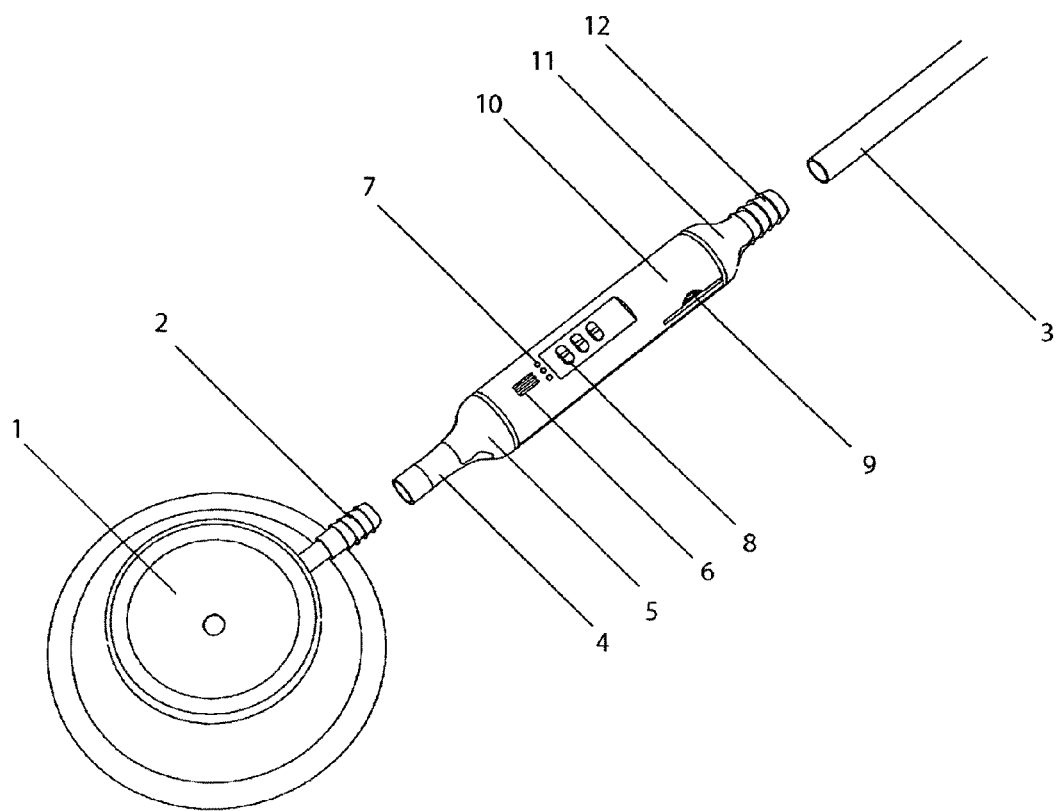
FIG. 1 is a perspective view of a first embodiment directed to an in-line device for reception between a stethoscope head and rubber tubing leading to the earpieces.
Figure 2:
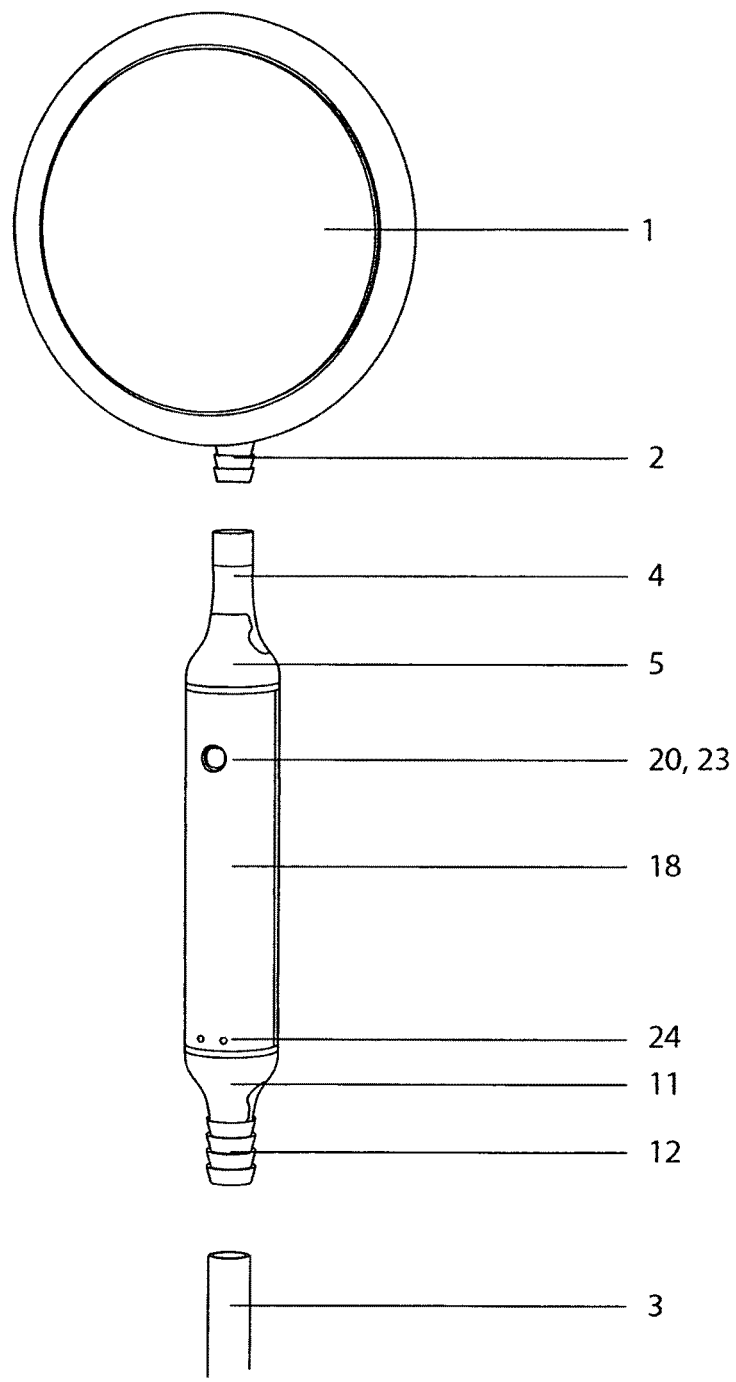
FIG. 2 is an upright perspective view of the first embodiment of FIG. 1.
Figure 3:
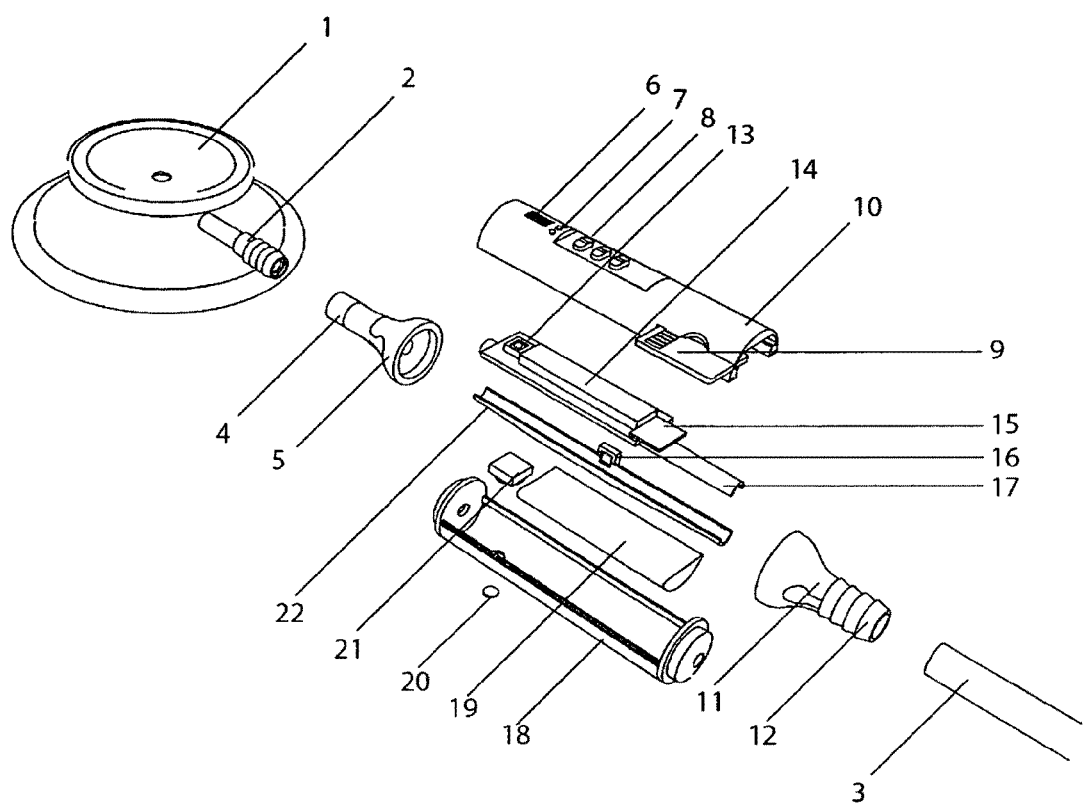
FIG. 3 is an exploded view of the first embodiment of FIGS. 1 and 2.

A third advantageous feature is that the diagnostic system remains agnostic of specific types of communication protocol, except that it favors a process of lightweight data transfer with minimized interference, and low power consumption Referring now to FIGS. 1-3, an in-line electronic recording device example according to a first embodiment of the invention comprises an upper housing part 10 and a lower housing part 18 together defining a housing within which is received an internal and external high dynamic range, low profile microphone 16 with acoustic noise cancelling, a CMOS fixed lens camera 21 (with lens 20), a short range wireless transceiver 14, a Solid State Disk (SSD) storage 9, an SSD interface 15, a top and bottom acoustic channel 17 and 22, a rechargeable battery 19, status LEDs 7, and power and activation buttons 8.

The device couples to the stethoscope in-line between the head 1 and the rubber tubing 3 leading to the conventional Y-split and earpiece (not shown). The device makes use of the internal high dynamic range, low profile microphone 16 to capture sound traveling through the stethoscope tube. The in-line construction advantageously has minimal impact on the acoustic properties of the stethoscope.

The in-line device (shown, for example, between the head 1 and the acoustic rubber tubing 3 in FIGS. 1 and 2) advantageously uses the external high dynamic range, low profile microphone 16 to capture sound clips from the head 1.

The device also optionally employs the low profile fixed lens CMOS camera 21 to capture subject photos.

The device is optionally equipped with an internal Solid State Disk (SSD) storage 9 and slot for removable storage. The recording device can also be equipped with a power source (for example, at least one rechargeable battery 19) and a low-power RF transceiver operating 14, for example, in the 2.4 GHz ISM band. Wireless communication is achieved, for example, using a standard protocol, such as BLUETOOTH, to enable the recording device to communicate with other electronic equipment. In order to conserve power, the device is advantageously activated by, for example, a pushbutton interface, allowing the user to control when segments of data are recorded and uploaded.

Adjustable or interchangeable rings on the recording device housing (acoustic rubber adapter 4, interface cap 5, interface cap 11, and acoustic rubber adapter 12) facilitate customized coupling to most common stethoscope head and tubing attachments. For example, acoustic rubber adapter 4 couples with a head connector 2 on the stethoscope head 1.

An audio microphone opening 6 is also advantageously provided in a convenient position communicative with a microphone 13 mounted within the space between top and bottom housing parts 10, 18, for example on the top housing part 10, as depicted, for allowing recording of voice or ambient sound data by the physician.

Figure 4:
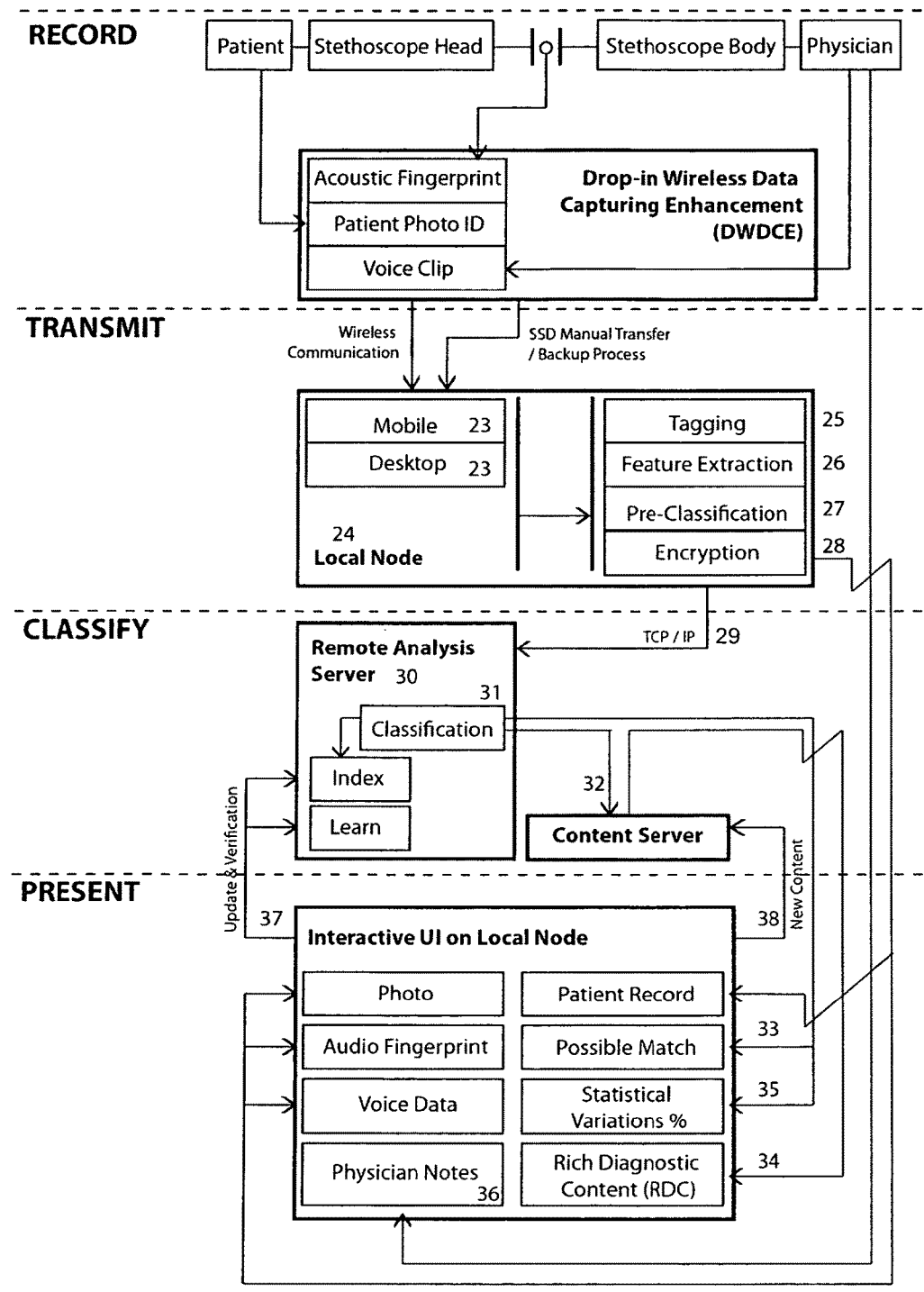
FIG. 4 is a system schematic operational flowchart of the first embodiment.
Figure 5:
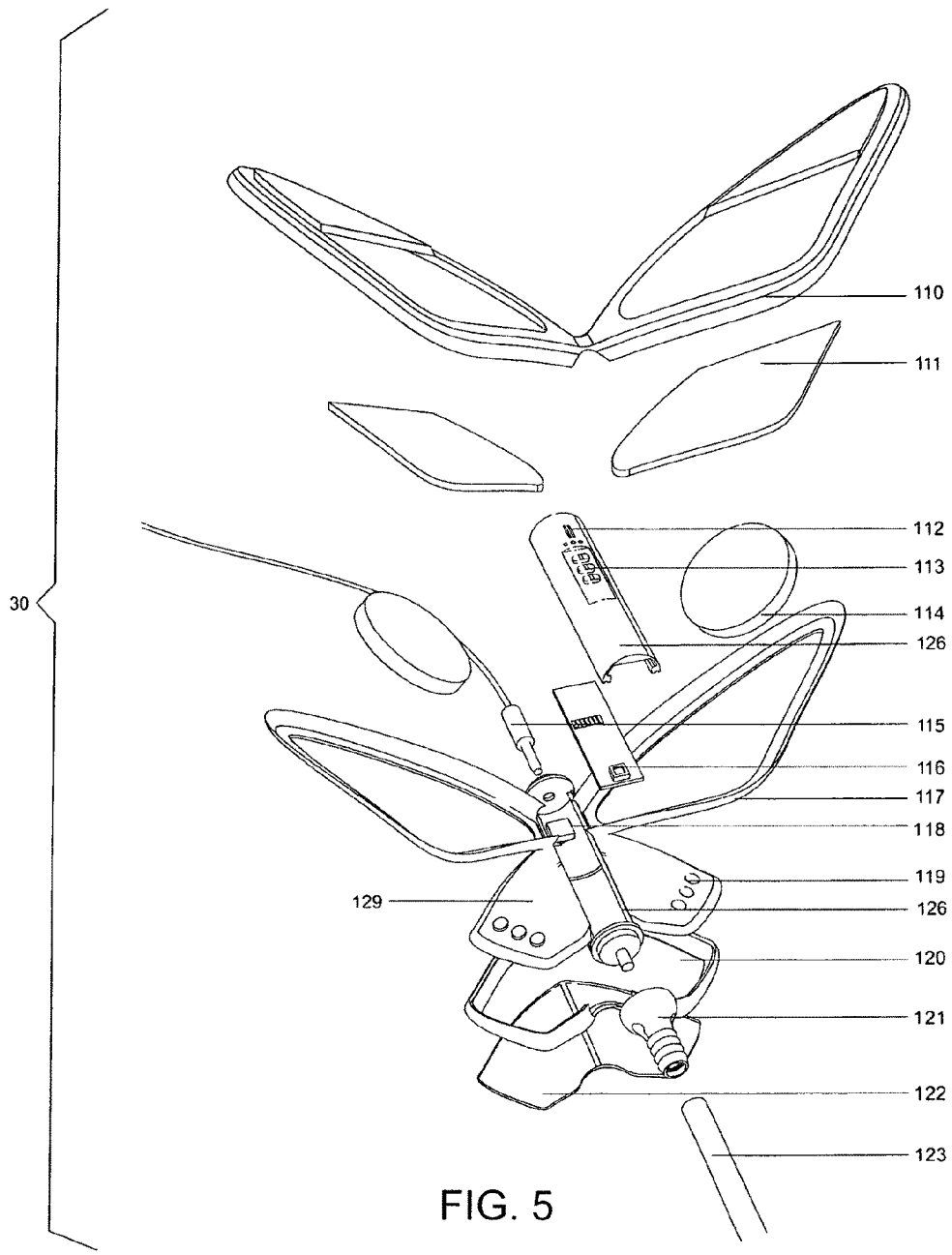
FIG. 5 is an exploded view of a stethoscope according to another embodiment of the invention having the appearance of a butterfly.
Figure 6:
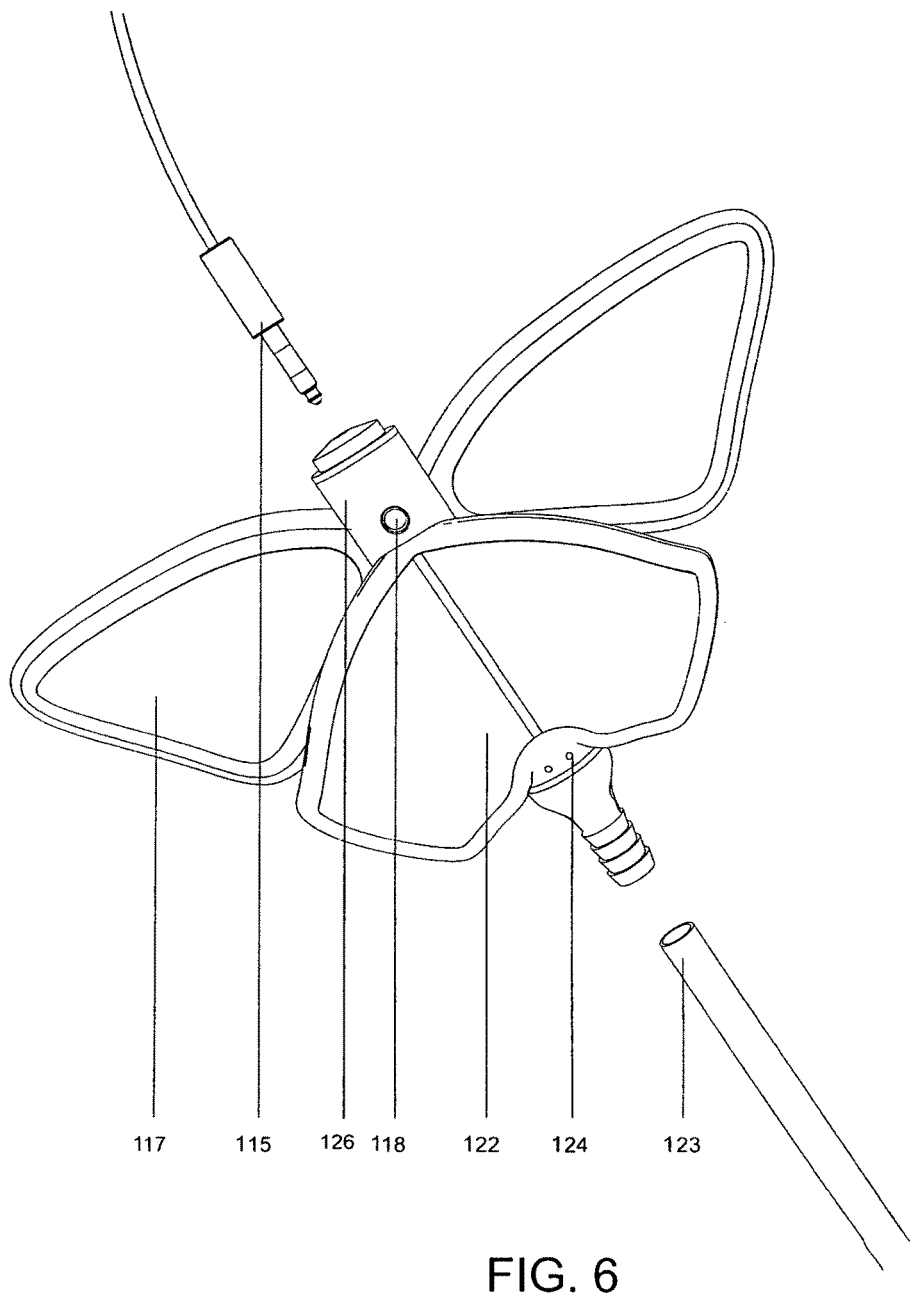
FIG. 6 is a perspective underside view of the stethoscope of FIG. 5.
Figure 7:
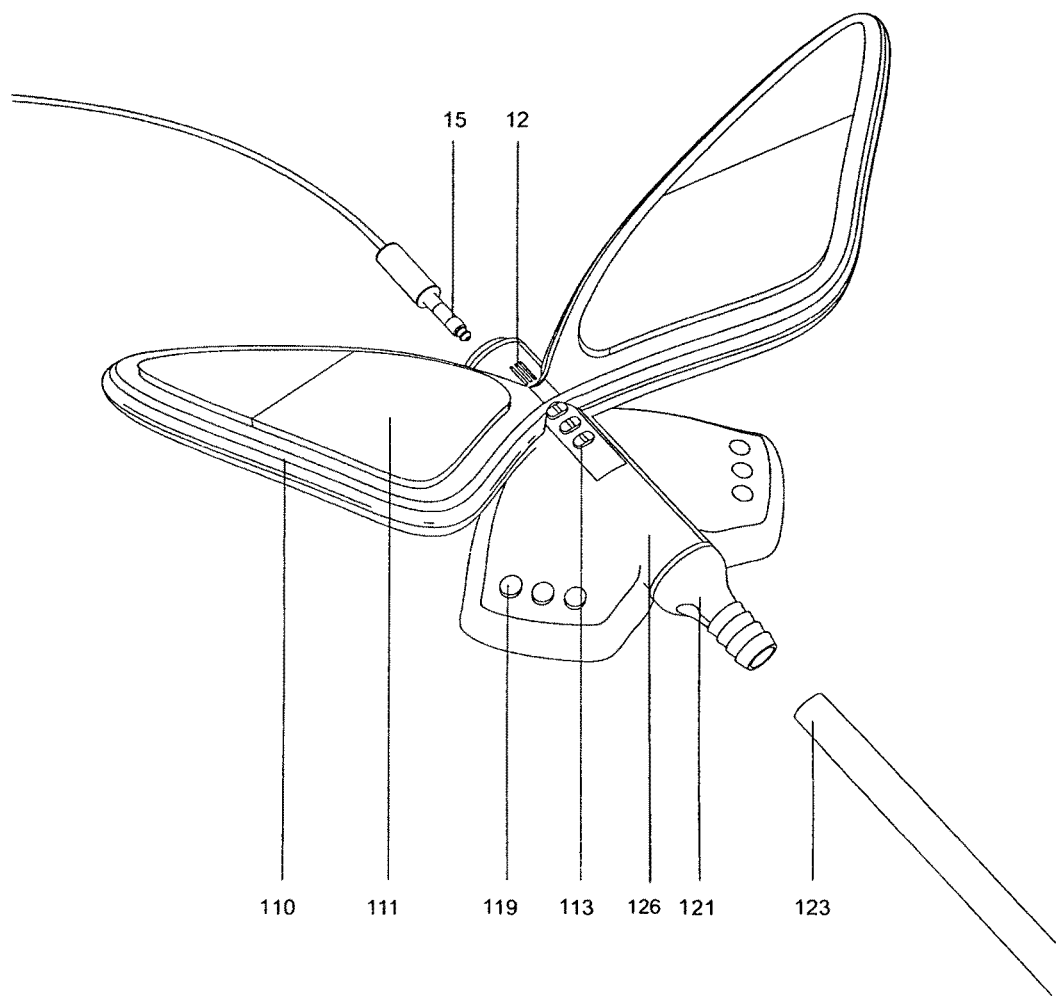
FIG. 7 is a perspective top view of the stethoscope of FIGS. 5 and 6.
Figure 8A:
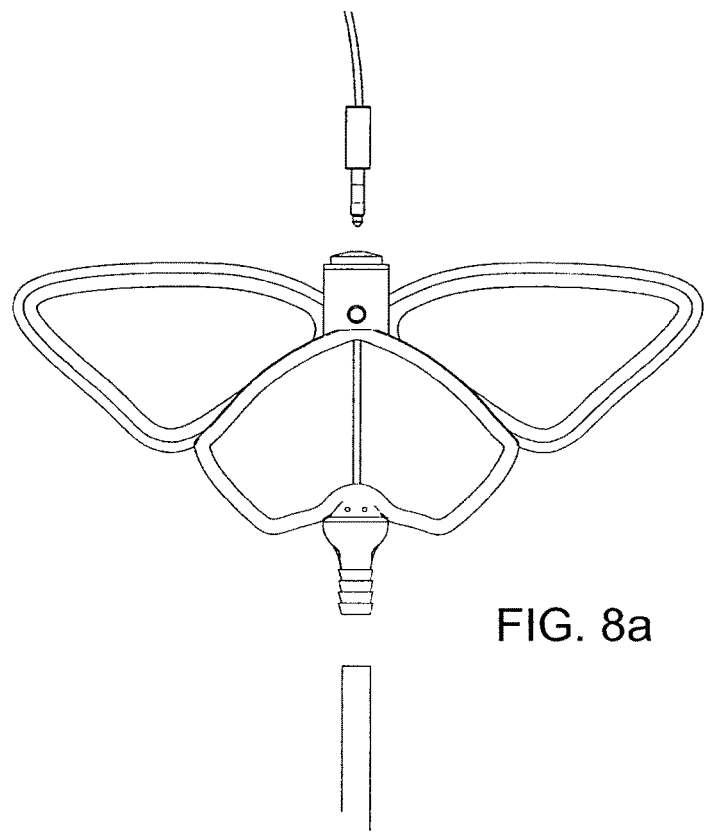
FIGS. 8a and 8b are bottom plan and side elevational views, respectively, of the stethoscope of FIGS. 5-7.
Figure 8B:
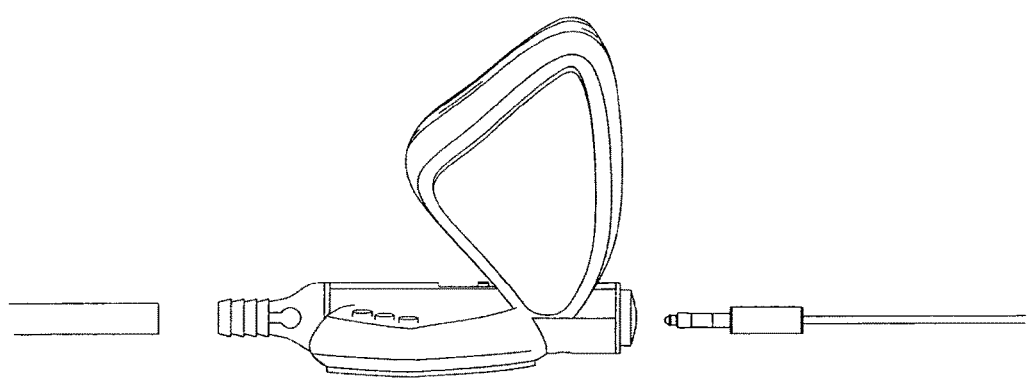
Figure 9A:
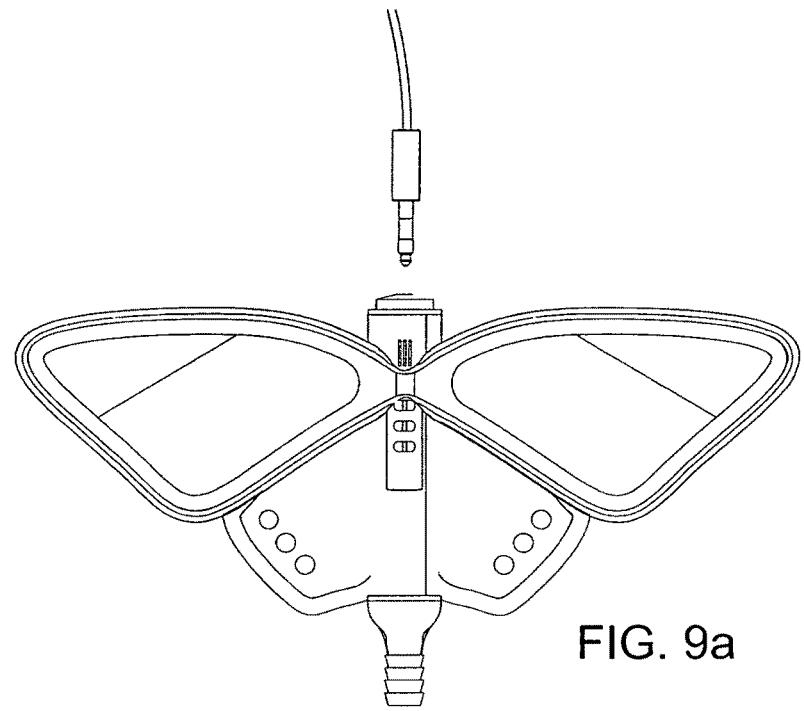
FIGS. 9a and 9b are top plan and rear elevational views, respectively, of the stethoscope of FIGS. 5-7.
Figure 9B:
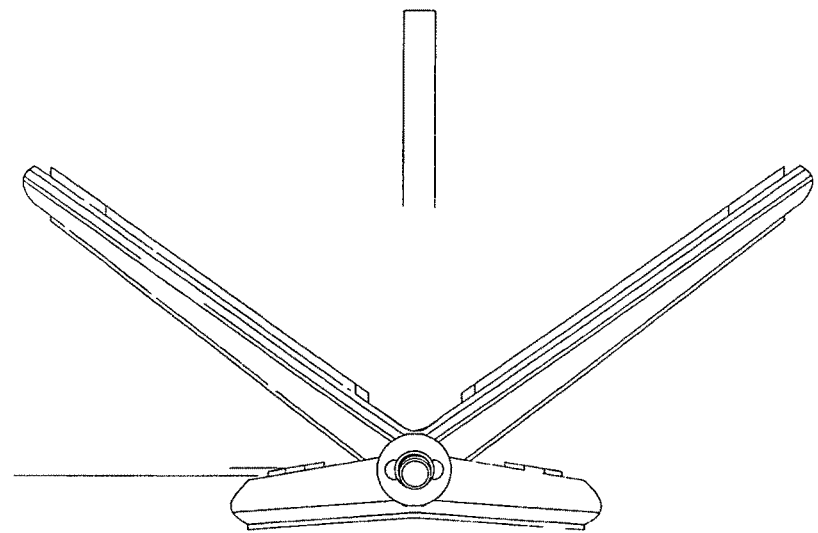

Referring to FIG. 4, a rich computing platform such as a mobile smartphone or laptop 23 (serving as part of a local computing node 24) communicates with the recording device using the 2.4 GHz wireless link, storing segments of audio data transmitted from the stethoscope. Local computing node 24 plays host to proprietary application software, which processes the recorded audio data. The processing at this level includes tagging 25, feature extraction 26, pre-classification of an acoustic fingerprint 27, and encryption 28.

Using a TCP/IP network 29, the local computing node 24 uploads secure encrypted data to a remote analysis server 30 running a classification engine 31. This software associates the acoustic fingerprint with a specific diagnosis, if possible. Based on the results, the local computing node 24 also links to the content server 32, which stores a database of RDC that may be pertinent to a diagnosis.

The diagnostic report 33 from the analysis server and the RDC 34 from the content server are sent back to the local computing node 24, where they are displayed in an interactive format.

Ambiguous results can be handled by displaying several different options and the statistical confidence levels 35 associated with each of them. RDC for several different medical conditions can also be aggregated in this type of report. Rather than relying on a machine algorithm with a single obscure output, the ability to display pertinent RDC inherently encourages the user to work iteratively to increase the level of confidence in the diagnosis. The fact that the RDC database is automatically indexed by recorded data sent from the stethoscope, means that diagnostic cues can also be delivered much more quickly than conventional methods.

In the case of a positive diagnosis verified by a registered physician, the local computing node 24 can be used to quickly update 37 the classification server. If desired, the associated audio fingerprint and raw audio signal can be integrated into the classification model as training data. Also, pertinent media 38 recorded by the physician at the time of diagnosis can optionally be added to the RDC database.

An advantageous embodiment of this invention functions as an acoustic pass-through, recording high dynamic range sound without altering the diagnostic integrity of the acoustic stethoscope's sound transmission. The device according to the embodiment captures sound through the unique arrangement of either an MEMS capacitive microphone, a piezoelectric microphone, or any other low profile, high dynamic range recording sensor.

Advantageously, the device in accordance with embodiment of the invention remains brand agnostic through use of a novel adaptor connector head on both the sound inlet and outlet, allowing for easy connectivity to virtually any acoustic stethoscope A distributed analysis system for automated delivery of Rich Diagnostic Content to conventional stethoscope users is also contemplated. The mechanism for distributed analysis offers unique and novel advantages in the mechanisms through which data is recorded, transmitted, classified and presented. The machine learning algorithm developed allows for a constantly updated or organic database and classification model, whereby the statistical relevance of the diagnostic response increases as a result of recurring feedback. The additional matching and delivery of the RDC further enhances the diagnostic process and patient experience.

During the capturing process, and advantageously as a direct benefit of the recent commercial introduction of MEMS microphones, fine sensing of high dynamic range sound (wherein the stethoscope produces mid to high frequency sound from the membrane, and low frequency from the bell) is achieved. The transmission part conveniently uses an existing wireless protocol and fingerprint recognition A diagnostic platform or database that "learns" through a unique algorithm and feedback mechanism is also contemplated, as discussed above with reference to FIG. 4.

The FDA regards this product as a Class I medical device, since its operation at no point affects, or has a life supporting role in, the patient treatment process. This makes time to market much faster, and hurdles to global expansion less strenuous.

The system contemplated herein advantageously requires three basic component elements, i.e., a suitable in-line recording and/or data capturing head, a classification database, and a computing node interface as either desktop or mobile application. While a specialized in-line recording and/or head can be developed by suitable known or future technologies for optimal performance, existing acoustic or electronic stethoscopes can be used to implement the method herein.

To build a suitable database for use with the disclosed system, the acoustic fingerprints required should advantageously be mapped in a controlled study within a research hospital, ideally by medical students. A diagnostic list needs to be formulated, and then sets of patients with known conditions at various ages advantageously need to be recorded. Every sample is then tagged with unidentifiable patient data, condition, and source location. After the base recordings are completed, a classification algorithm will be built using this data. This can be done in-house with the assistance, for example, of programmers, a sound engineer, and a UI/web designer.

Once the database is in place, the UI (user interface) and software design for a computing node can be developed to leverage this classification engine in the three product use cases previously mapped out. The interface should present the patient photo, digital medical record, acoustic signature, classification response and variations (if applicable, rich diagnostic content, doctors audio note and commentary) and/or video.

Licensing of the database to other diagnostic product companies, future sale of database, subscription for database usetiered pricing for urban, rural, academic and the developed world, is also contemplated within the scope of the invention.

A further embodiment is directed to another type processing device-equipped stethoscope, advantageously connectable with the acoustic rubber tube 3 of a standard acoustic stethoscope, and integrates an in-line device along the lines of the previously described device embodiment and a head. Such embodiment is shown by way of example in FIGS. 5-8, wherein such device assumes the general form of a butterfly so as to be particularly well suited for use in pediatric medicine, as will be described in detail below.

An example of the invention according to such embodiment will be described with reference to FIGS. 5-9b. A stethoscope embodied to resemble a butterfly is generally designated by the numeral 30. A head of the stethoscope 30 includes a central body 126, within which a circuit substrate having a MEMS microphone 116 mounted thereto along with any required circuitry (digital processing, amplification means, etc.). A wing casing 110 (defining a pair of front, larger wings) extends from the central body 126, within which one or more batteries 114 are housable. A pair of display screens 111 (OLED, LCD or the like) can optionally be provided to face outward of the wing casing 110 to allow display of visual effects, information, pictures, logos or data, etc. A wing lower closure 117 encloses a chamber within the wing casing 110, in which the one or more batteries are housable.

A pair of rear, smaller wings defined by a rear wing casing 129 enclose a sound chamber 120 which adjoins a membrane 122 for detecting patient sounds in the manner of a conventional stethoscope head membrane, and which delimits the sound chamber at a side thereof facing a patient when the stethoscope 30 is being used to collect patient data. The sound camber is in direct communication with an interior chamber of the central body, in which is housed the aforementioned MEMS microphone 116, thereby allowing accurate recording of the sounds collected by the membrane 122.

In an embodiment having analog acoustic capabilities, such as that shown in the depicted example, a stethoscope acoustic tube adapter 121 is provided in a rear position of the butterfly-shaped structure to which an acoustic tube 123, leading to the ears to the physician (for example, in a conventional manner), is receivable.

An audio microphone 112 is also advantageously provided in a convenient position, for example on a top of the central body 126, for allowing recording of voice or ambient sound data by the physician, for a more complete examination record.

Various other features are conveniently provided at the central body 126. For example, operation buttons and indicator LEDs 113 to allow effective user interface for selecting desired functional modes, adjusting recording levels, etc., are advantageously provided on a top position of the central body 126 to permit convenient access by the physician during use of the stethoscope 130. A camera 118, advantageously directed from a bottom of the central body 126, permits the taking of patient and other relevant photos at a time of measurement (or before or after), to assemble a more complete patient history and allow better remote evaluation of audio data collected.

An electronic line-out 115 is optionally provided, conveniently positioned at a forward end of the central body, for output of collected electronic data, including, but not limited to, the audio signals produced by the MEMS microphone 116, audio data collected by the audio microphone 112, camera images collected by camera 118, etc. While depicted as having a phone jack type connector for stereo output of audio signals in the illustrative example, the line-out 115 can alternatively be a USB or like port for transmission of any form of digital data collected by the various components of the head of the stethoscope 30. Such digital data is transmittable remotely of the stethoscope directly for analysis of the signals by comparison with a database of illnesses or conditions, or to a memory media for storage and later comparison with the collected data in a database. The line-out 115, when optionally fashioned as a data connection (USB or the like), can then optionally also serve as a line-in for programming circuitry housed the head of stethoscope 30 and/or for receiving a tentative evaluation after comparison with the database, for display on the display screens 111 or as audio output to the physician via, for example, the acoustic tube 123.

Additional or alternative operation buttons 119 are optionally provided on the rear wings for ready access.

Figure 10:
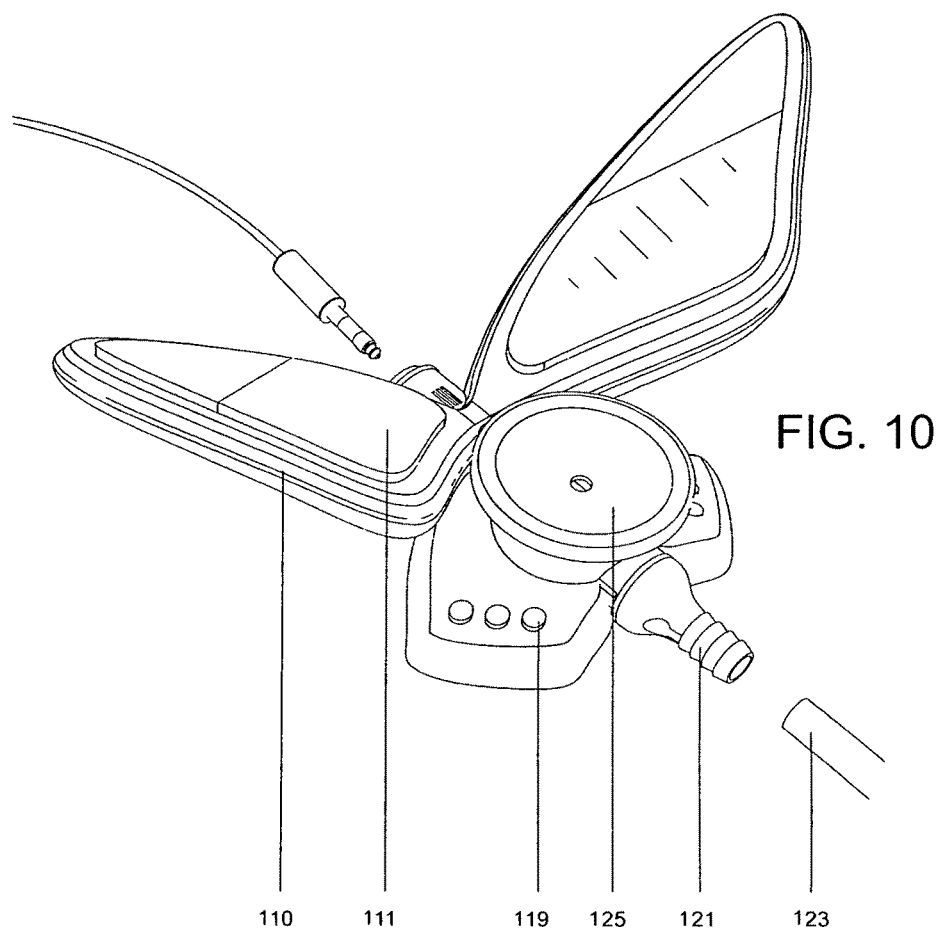
FIG. 10 is a perspective top view of another embodiment according to the invention which incorporates a low frequency bell alternative.

Turning now to FIG. 10, another embodiment in which a low frequency bell 125 is provided in addition to, or in place of, some of the components described with reference to the previous embodiment, in the positional placement conveniently as shown. The an interior chamber delimited by the membrane of the bell 125 is in direct communication with (i.e., open to) the interior chamber of the central body 126 in which is housed the aforementioned MEMS microphone 116, for accurate recording and also proper transmission of the analog acoustics through the tube 123.

Figure 11A:
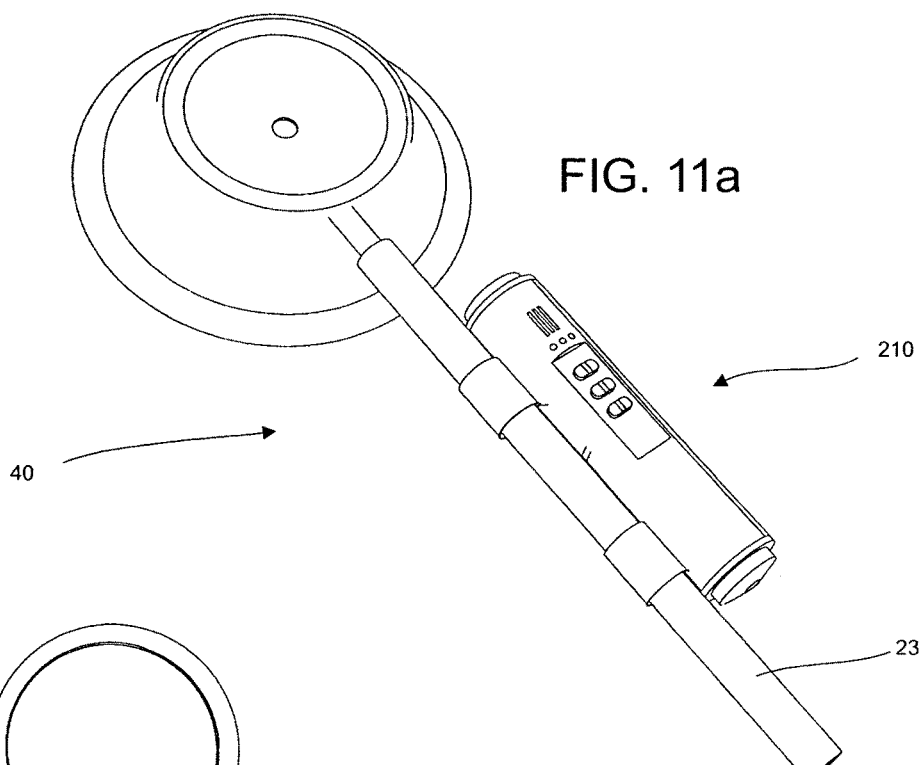
Figure 11A:
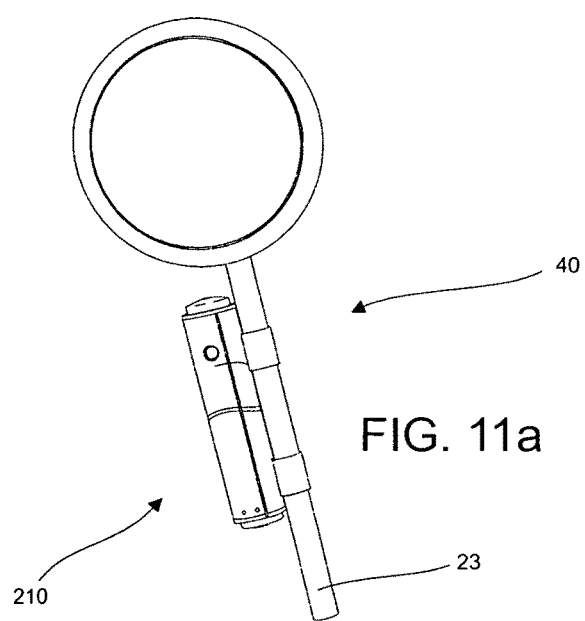

Referring now to FIGS. 11a, 11b, 12a and 12b, alternative embodiments directed to a camera module receivable to a conventional stethoscope. The concept of having a camera in close reach of a physician is considered particularly advantageous, as already mentioned herein. FIGS. 11a and 11b depict an embodiment in which a removable camera module 210 having a camera component analogous with the embodiment of FIGS. 5-9b, is received to an acoustic tube 23 of a conventional stethoscope 40. In this embodiment, no special appearance is imparted to the camera 210, such as the butterfly of the previously described examples.

Figure 12A:
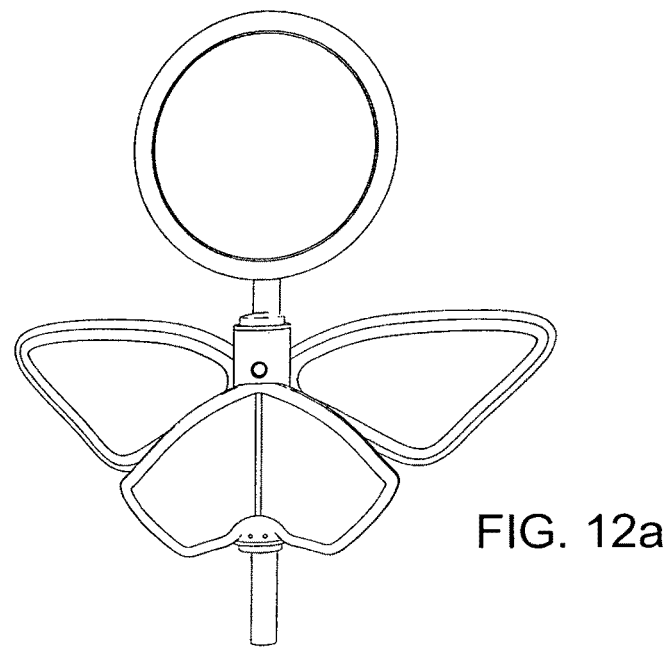
FIGS. 12a and 12b are a top plan view and a perspective view of another embodiment which includes clip-on camera for attachment to a conventional stethoscope embodied in a form of a butterfly.
Figure 12B:
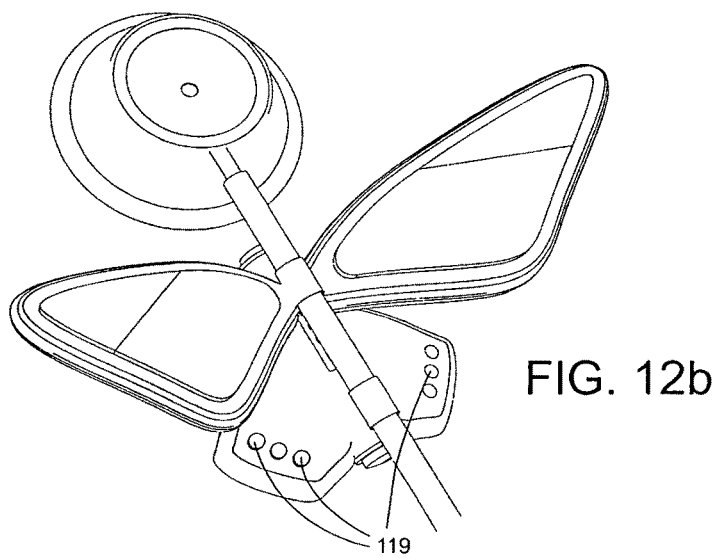

Another of the camera module embodiments according to the invention is shown in FIGS. 12a and 12b. This embodiment differs from that of FIGS. 11a and 11b, insofar as a structural configuration resembling a butterfly is provided in addition to the basic camera module (with the attendant advantages already mentioned, such as the wing compartment for battery, etc.), and in which it is also possible, as shown, to optionally have operation buttons (119, described previously) on the rear wings for ready access by the physician.

FIG. 13 illustrates a possible form of decoration which can be present on the wing casing 110 and rear wing casing 129, in the depiction mimicking a Monarch butterfly. Such pattern is advantageously colorful, so as to elicit a response of interest and curiosity on the part of the patient being examined (for example a child) rather than one of generalized anxiety and trepidation often precipitated in a clinical environment of an examining room.

As previously described, the central body of the butterfly stethoscope 30 is equipped to carry out a plurality in functions, including a flashlight, sound recognition for diagnostic modality, video recording, voice recording, memory chips, camera for identification and documentation purposes. As shown in FIG. 13, an optional laser pointer is included. As shown in FIG. 14, additionally, an optional pocket clip can be provided on the central body.

One end of the central body is connected to the ear phones 131 (as shown in FIGS. 13 and 16b, where they appear as the antennae of a butterfly) or to the ear piece of a regular stethoscope (as shown in FIG. 16a). The other end is blind, at which end can optionally be provided a laser pointer or flashlight.

The wings can serve various desired functions, as depicted in FIGS. 13-16b. The front ones of the wings (defined by wing casing 110) can advantageously be configured to flip upward to facilitate grasping of the device, as depicted in FIG. 15. The wings can optionally display a logo, a name, an ID, an animated light, etc.

The rear ones of the wings (smaller ones in the figures, as defined by rear wing casing 129) can accommodate sound detectors (i.e., membranes 122) Therefore, the wings defined by the rear wing casing 129 are advantageously always horizontally flat so as to rest against the body part (chest, heart area, abdomen, etc.). Of course, it will be recognized that alternatively, the rear wings can carry the low frequency membrane and the front wings can carry the high frequency membrane. In that case the front wings will remain flat and the device can be held with a ring device attached to anterior part of the body piece). The sound is transmitted from the rear wings to the body from the lateral sides of the body.

Alternatively, the listening device can comprise one or more microphones 130 having suitable sensitivity and frequency ranges, which capture the sounds as electronic signals, as shown in FIG. 14.

As shown in FIG. 16a, it is contemplated that the butterfly stethoscope can be embodied for use with an acoustic earpiece of a standard acoustic stethoscope (as shown in the depiction of FIG. 16a) in which case, if the sounds are captured by electronic means, such as with a microphone, the in-line device will additionally include a speaker for reproducing the electronic data into audio, so that the physician can here the sounds while simultaneously recording and sending the digital electronic data for analysis and/or storage for future use.

Alternatively, the butterfly sensor assembly can send electronic information to ear buds 131 which convert the data to audible sound, as shown in FIG. 16b. As also shown, the ear buds optionally include a pair of magnets 132 on a back portion thereof (advantageously shielded from the speakers in the earpieces so as not to adversely interfere with sound reproduction), so that when not in active use, the stethoscope can be worn as a necklace or hanging pendent by affixing the magnets, one to the other, behind the neck of the physician or diagnostician.

While, for depiction and illustrative purposes herein, the selected examples are all butterfly likenesses, it is contemplated that any animal or other character or cartoon likeness, real or imaginary which is perceived positively, particularly by children, is employable in place of a butterfly. For example, as shown in the various depictions of FIG. 17, the stethoscope head (or in-line device) could be fashioned as a lizard, frog, hummingbird, clown, lion, mouse, fish, etc., or a well known cartoon or comics characters without departure from the invention.

Furthermore, other representations of familiar icons can be adopted in the design appearance of a device in accordance with the invention. FIGS. 18-21b depict an example in which a stethoscope head is made to resemble a heart shaped icon. Functionality and various components are analogous with those of the embodiment of FIGS. 13-16b, and therefore have not been repeated.

For purposes herein, the term "icon" refers collectively to all shapes which bear resemblance to any familiar subject, including any of the aforementioned examples, including animals, characters and design shapes.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. A method of analyzing data from a stethoscope having a head configured to obtain acoustic chest sounds from a patient's chest, an in-line body defining an acoustic channel between a first end connected to the head, receiving said acoustic chest sounds and transmitting them without any electronic processing to a second end, said stethoscope further including an acoustic sound receiver attached to the second end and arranged to transmit the acoustic chest sounds to the user of the stethoscope, the in-line body further including an electronic microphone generating electronic chest signals corresponding to the digital signal, the in-line body further including a digital camera arranged and constructed to take a digital picture of the patient whose chest is being examined, the method comprising:
   Placing the head of the stethoscope against the chest of the patient to obtain acoustic chest sounds;
   Transmitting the acoustic chest sounds through said in-line body to the acoustic sound receiver to allow the stethoscope user to listen to said acoustic chest sounds;
   Converting said acoustic chest sounds by said microphone into an acoustic fingerprint of the patient;
   Taking a digital picture of the patient;
   assembling a data segment including the digital picture of the patient and the acoustic fingerprint of the patient;
   transmitting said data segment to a remote analysis server.

2. A method according to claim 1, wherein:
   a local computing node encrypts said data segment into an encrypted segment; and
   said local computing node data is uploaded as secure encrypted data.

3. A method according to claim 2, further comprising processing said digital data in said local computing node, said processing including tagging, feature extraction, pre-classification of an acoustic fingerprint and encryption.

4. A method according to claim 1, further comprising associating said acoustic fingerprint with a database of stored acoustic fingerprints to yield a report of at least one suspected diagnosis for the patient as identified by the digital image by use of said classification engine; and incorporating said suspected diagnosis into said data segment.

5. A method according to claim 1, further comprising:
   Receiving a report providing a diagnosis for the patient; and
   displaying the report to the user.

6. A method according to claim 5, wherein said displaying includes displaying different options and the statistical confidence levels associated respectively therewith.

7. A method according to claim 5, further comprising:
   updating the analysis server upon a positive diagnosis verified by a registered user of the method.

8. A method according to claim 7, further comprising:
   adding pertinent media recorded by the user, at the time of the positive diagnosis, to the database.

9. The method of claim 1 wherein said remote analysis surver is running a classification engine, said digital data being associated to the patient by the digital image.

10. The method of claim 9 further comprising receiving a user voice signal from the user, and incorporating said voice signal into said data segment.

11. A stethoscope comprising:
   a head arranged and constructed to detect chest sound waves when placed against the chest of a patient;
   a housing having a first end connected to said head and a second end connected to an earpiece, said housing being arranged and constructed to form an acoustic channel and transmit said chest sound waves from said first to said second end;
   an acoustic receiver attached to said second end and receiving said chest sound wave for analysis locally by a physician;
   a digital camera disposed on said housing and arranged and constructed to capture digital images of the patient;
   an electronic microphone disposed in said housing and arranged to convert said chest sound waves into electronic chest sound waves;
   a signal processor disposed in said housing and arranged to generate a digital data segment including a digital image of the respective patient for identifying the patient and an acoustic fingerprint derived from said electronic sound waves and transmit said digital data segment to a remote location.

12. A stethoscope attachment according to claim 11, wherein an exterior of said housing is configured to resemble or give a visual impression of an icon of pleasing appearance.

13. A stethoscope according to claim 12,
   wherein said icon is a butterfly, bird or heart shape.

* * * * *